United States Patent
Ben-Attar et al.

(10) Patent No.: US 7,596,503 B2
(45) Date of Patent: Sep. 29, 2009

(54) ADVERSE DRUG REACTION REDUCTION

(75) Inventors: Emile Ben-Attar, Nof Ayalon (IL); Ran Rayter, Ramat HaSharon (IL)

(73) Assignee: Mirik Medical Ltd., Ramat Gan (IL)

( * ) Notice: Subject to any disclaimer, the term of this patent is extended or adjusted under 35 U.S.C. 154(b) by 0 days.

(21) Appl. No.: 11/766,388

(22) Filed: Jun. 21, 2007

(65) Prior Publication Data

US 2008/0010088 A1    Jan. 10, 2008

Related U.S. Application Data

(60) Provisional application No. 60/815,999, filed on Jun. 22, 2006.

(51) Int. Cl.
*A61B 5/00* (2006.01)
*G06F 19/00* (2006.01)
(52) U.S. Cl. .................................... 705/3; 705/2; 705/4
(58) Field of Classification Search ................. 705/2–4
See application file for complete search history.

(56) References Cited

U.S. PATENT DOCUMENTS

| | | | | |
|---|---|---|---|---|
| 5,737,539 | A | * | 4/1998 | Edelson et al. .................. 705/3 |
| 5,845,255 | A | * | 12/1998 | Mayaud ........................ 705/3 |
| 6,654,724 | B1 | | 11/2003 | Rubin et al. |
| 6,680,999 | B1 | | 1/2004 | Garcia |
| 6,776,341 | B1 | * | 8/2004 | Sullivan et al. ........ 235/462.01 |
| 6,915,265 | B1 | * | 7/2005 | Johnson ........................ 705/2 |
| 6,994,249 | B2 | * | 2/2006 | Peterka et al. .............. 235/375 |
| 2002/0111829 | A1 | | 8/2002 | Robibero | 
| 2003/0080191 | A1 | * | 5/2003 | Lubow et al. ........... 235/462.01 |
| 2003/0083769 | A1 | * | 5/2003 | Yamazaki .................... 700/116 |
| 2003/0140928 | A1 | * | 7/2003 | Bui et al. ..................... 128/898 |
| 2004/0099683 | A1 | * | 5/2004 | Shows et al. ................. 221/263 |
| 2005/0033606 | A1 | * | 2/2005 | Miller ........................... 705/2 |
| 2005/0060197 | A1 | * | 3/2005 | Mayaud ......................... 705/2 |
| 2005/0154627 | A1 | | 7/2005 | Zuzek et al. |

(Continued)

OTHER PUBLICATIONS

Gronroos et al., "A medication database—a tool for detecting drug interactions in hospital", Eur J Clin Pharmacol (1997) 53: 13-17.*

(Continued)

*Primary Examiner*—C. Luke Gilligan
*Assistant Examiner*—Neal R Sereboff
(74) *Attorney, Agent, or Firm*—Darby & Darby P.C.

(57) ABSTRACT

Apparatus is provided, including an adverse drug reaction (ADR) control server (3) including a processor and a data port. The server is configured to receive from a user (20), via the data port, in a first interaction with the user, a list of one or more current medications, and to send to the user a first medication code responsively to the list. In a second interaction with the user, the server receives the first medication code from the user and an indication of a new medication. The server accesses, by the processor, the list of one or more current medications based on the received first medication code, and generates an adverse drug reaction (ADR) warning based on the list of one or more current medications and the new medication. The server sends the user a new medication code based on the list of one or more current medications and the new medication. Other embodiments are also described.

10 Claims, 5 Drawing Sheets

U.S. PATENT DOCUMENTS

| | | | |
|---|---|---|---|
| 2005/0187792 | A1 | 8/2005 | Harper |
| 2005/0216313 | A1 | 9/2005 | Claud et al. |
| 2006/0041330 | A1* | 2/2006 | Ansari et al. ............... 700/240 |
| 2006/0054682 | A1* | 3/2006 | de la Huerga ............... 235/375 |
| 2007/0095850 | A1* | 5/2007 | Meyer ........................... 221/2 |
| 2008/0020018 | A1* | 1/2008 | Moodley et al. ............ 424/433 |

OTHER PUBLICATIONS

Preventable Adverse Drug Reactions: A Focus on Drug Interactions (http://www.fda.gov/cder/drugReactions/default.htm).

U.S. Appl. No. 60/815,999, filed Jun. 22, 2006.

http://www.fda.gov/cder/drug/drugReactions/default.htm.

Commitee on Quality of Health Care in America: Institute of Medicine. To err is human: building a safer health system. Washington, D.C: National Academy Press; 2002.

Leape LL et al. The nature of adverse events in hospitalized patients. Results of the Harvard Medical Practice Study II. N Engl J Med 1991; 324(6):377-384.

Classen DC et al. Adverse drug events in hospitalized patients. Excess length of stay, extra costs, and attributable mortality. JAMA 1997; 277(4): 301-306.

Schappert SM. Ambulatory care visits to physician offices, hospital outpatient departments, and emergency departments: United States, 1997. National Center for Health Statistics. Vital Health Stat. 1999; 13(143).

Jacubeit T et al. Risk factors as reflected by an intensive drug monitoring system. Agents Actions 1990; 29: 117-125.

Leape LL et al. Systems analysis of adverse drugs events. ADE Prevention Study Group. JAMA 1995; 274(1):35-43.

Raschetti R et al. Suspected adverse drug events requiring emergency department visits or hospital admissions. Eur J Clin Pharmacol 1999; 54(12);959-963.

Bates DW et al. Effects of computerized physician order entry and a team intervention on prevention of serious medication errors.JAMA 1998; 280(15):1311-1316.

Smalley W, Shatin D, Wysowski DK, Gurwitz J Andrade SE, Goodman M, et al. Contraindicated use of cisapride: impact of food and drug administration regulatory action. JAMA 2000; 284(23):3036-3039.

Evans RS, Pestotnik SL, Classen DC, Horn SD, Bass SB, Burke JP. Preventing adverse drug events in hospitalized patients. Ann Pharmacother 1994;28(4):523-527.

Manasse HR Jr. Medication use in an imperfect world: drug misadventuring as an issue of public policy, Part 1. Am J Hosp Pharm. May 1989; 46(5)929-44.

M. Saginur, et al. "The uptake of technologies designed to influence medication safety in Canadian hospitals", Journal of Evaluation in Clinical Practice 14 (2008) 27-35.

David H. Kreling, et al., "Community pharmacist's work environments: evidence from the 2004 national pharmacist workforce study", Journal of the American Pharmacists Association, vol. 47, No. 5, 2006.

* cited by examiner

ADVERSE DRUG REACTION REDUCTION

CROSS-REFERENCES TO RELATED APPLICATIONS

The present patent application claims the benefit of U.S. Provisional Patent Application 60/815,999 to Ben-Attar et al., filed Jun. 22, 2006, entitled, "Adverse drug reaction reduction," which is incorporated herein by reference.

This application is related to a PCT patent application, entitled, "Adverse drug reaction reduction," which is filed on even date herewith and is incorporated herein by reference.

FIELD OF THE INVENTION

The present invention relates generally to reducing adverse drug reactions, and specifically to methods and algorithms for reducing adverse drug reactions such as adverse drug-to-drug interactions.

BACKGROUND OF THE INVENTION

Drug therapy complications are common in the ambulatory setting and often lead to hospitalization. Between 5 and 10 percent of all hospital admissions in the United States have been attributed to a drug therapy complication. Among the elderly, this figure has been reported to be between 10 and 30 percent. In one report, the overall direct cost of admissions to hospitals or long-term care facilities due to noncompliance were estimated to be approximately $30 billion a year, the indirect cost estimate exceeded $50 billion annually (Task Force for Compliance 1993). A six-month study of adverse drug events at Brigham and Women's Hospital and Massachusetts General Hospital in Boston disclosed that errors occurred at every point in the medication use process, from the initial order (49 percent of errors) through transcription (11 percent), dispensing (14 percent), and administration of medication (26 percent). When one considers that approximately 3.75 billion drug administrations (Manasse 1989) are made annually to patients in U.S. hospitals, with 20 steps per administration, the opportunities for things to go wrong are considerable.

Leape et al. (1995) examined the data from the Brigham and Women's Hospital and the Massachusetts General Hospital study and identified 16 major system failures that could lead to treatment errors and drug therapy complications. Many of these failures were attributed to one or both of two basic problems:

Failures in communication, particularly in the transfer of drug and/or patient information from one health care provider to another, leading to incorrect therapeutic decisions based on incomplete information; and Inadequate information, leading to errors in drug choice, dosage, timing, and administration.

The US Food and Drug Administration (FDA) in collaboration with the Center for Education and Research on Therapeutics have developed a module termed Preventable Adverse Drug Reactions: A Focus on Drug Interactions (http://www-.fda.gov/cder/drug/drugReactions/default.htm), which is incorporated herein by reference. This report regarding hospitalized patient populations estimates that 6.7% of hospitalized patients have a serious adverse drug reaction, with a fatality rate of 0.32%. If this estimate is correct, then there are more than 2 million serious adverse drug reactions (ADRs) in hospitalized patients, causing over 100,000 deaths annually. If true, then ADRs are the 4th leading cause of death—ahead of pulmonary disease, diabetes, AIDS, pneumonia, accidents, and automobile deaths.

These statistics do not include the number of ADRs that occur in ambulatory settings. Also, it is estimated that over 350,000 ADRs occur in U.S. nursing homes each year. Approximately two thirds of all patient visits to physicians result in prescriptions, and the rate of ADRs increases substantially after a patient is taking four or more medications. The exact number of ADRs is not certain and is limited by methodological considerations. However, whatever the true number is, ADRs represent a significant public health problem that is, for the most part, preventable.

Recent publications have shown that many adverse drug reactions can be prevented and detected through the use of systems interventions. For example, many health systems have instituted new technologies to minimize patient injury due to medication errors and drug-drug interactions. Tools like computerized physician order and prescription entry and bar coding systems have demonstrated tangible benefits. The potential for reducing medication errors by using computerized medical records as well as drug-interaction screening software that detects and alerts the physician and/or pharmacist to potentially serious drug interactions has been recognized.

The following references are related to this discussion, and are incorporated herein by reference:

Committee on Quality of Health Care in America: Institute of Medicine. To err is human: building a safer health system. Washington, D.C.: *National Academy Press;* 2000.

Lazarou J et al. Incidence of adverse drug reactions in hospitalized patients: A meta-analysis of prospective studies. *JAMA* 1998; 279:1200-1205.

Gurwitz J H et al. Incidence and preventability of adverse drug events in nursing homes. *Am J Med* 2000; 109(2):87-94.

Johnson J A et al. Drug-related morbidity and mortality. A cost-of-illness model. *Arch Intern Med* 1995; 155(18):1949-1956.

Leape L L et al. The nature of adverse events in hospitalized patients. Results of the Harvard Medical Practice Study II. *N Engl J Med* 1991; 324(6):377-384.

Classen D C et al. Adverse drug events in hospitalized patients. Excess length of stay, extra costs, and attributable mortality. *JAMA* 1997; 277(4):301-306.

Schappert S M. Ambulatory care visits to physician offices, hospital outpatient departments, and emergency departments: United States, 1997. National Center for Health Statistics. *Vital Health Stat.* 1999; 13(143).

National Association of Chain Drug Stores. 2000 community pharmacy results. 2001. Alexandria, Va.

Jacubeit T et al. Risk factors as reflected by an intensive drug monitoring system. *Agents Actions* 1990; 29:117-125.

Leape L L et al. Systems analysis of adverse drug events. ADE Prevention Study Group. *JAMA* 1995; 274(1):35-43.

Raschetti R et al. Suspected adverse drug events requiring emergency department visits or hospital admissions. *Eur J Clin Pharmacol* 1999; 54(12):959-963.

Bates D W et al. Effect of computerized physician order entry and a team intervention on prevention of serious medication errors. *JAMA* 1998; 280(15):1311-1316.

Evans R S, Pestotnik S L, Classen D C, Horn S D, Bass S B, Burke J P. Preventing adverse drug events in hospitalized patients. *Ann Pharmacother* 1994; 28(4):523-527.

Gebhart F. VA facility slashes drug errors via bar-coding. *Drug Topics* 1999; 1:44.

Committee on Quality of Health Care in America: Institute of Medicine. To err is human: building a safer health system. Washington, D.C.: National Academy Press, 2000.

Cavuto N J, Woosley R L, Sale M. Pharmacies and prevention of potentially fatal drug interactions. *JAMA* 1996; 275: 1086-1087.

Smalley W, Shatin D, Wysowski D K, Gurwitz J Andrade S E, Goodman M, et al. Contraindicated use of cisapride: impact of food and drug administration regulatory action. *JAMA* 2000; 284(23):3036-3039.

Manasse H R Jr. Medication use in an imperfect world: drug misadventuring as an issue of public policy, Part 1. Am J Hosp Pharm. 1989 May; 46(5):929-44.

Manasse H R Jr. Medication use in an imperfect world: drug misadventuring as an issue of public policy, Part 2. Am J Hosp Pharm. 1989 May; 46(5):1141-52.

SUMMARY OF THE INVENTION

There is provided, in accordance with an embodiment of the invention, a method, including:

(a) in a first interaction with a user, electronically receiving from the user a list of one or more current medications; and electronically sending to the user a first medication code responsively to the list;

(b) in a second interaction with the user, electronically receiving the first medication code from the user and an indication of a new medication;

(c) electronically accessing the list of one or more current medications based on the received first medication code, and generating an adverse drug reaction (ADR) warning based on the list of one or more current medications and the new medication; and (d) electronically sending the user a new medication code based on the list of one or more current medications and the new medication.

In an embodiment, sending the first medication code to the user includes determining whether a medication code already exists with respect to the list, and, if so, sending the already-existing medication code to the user, and, if not, generating the first medication code and sending the generated first medication code to the user.

In an embodiment, generating the first medication code includes generating the code not responsively to a pharmaceutical characteristic of at least one of the current medications.

In an embodiment:

receiving the list from the user includes receiving an indication of a dosage of at least one of the current medications, sending the first medication code includes sending the first medication code responsively to the list and the dosage, accessing the list includes accessing the list and the dosage, and generating the ADR warning includes generating the ADR warning based on the list, the new medication, and the dosage.

In an embodiment, sending the first medication code responsively to the received indication of the dosage includes:

if the dosage is near a dosage of the one of the current medications for which a medication code has already been generated, sending as the first medication code the same medication code that has already been generated; and if the dosage is not near a dosage of the one of the current medications for which a medication code has already been generated, sending as the first medication code a medication code different from the medication code that has already been generated.

There is also provided, in accordance with an embodiment of the invention, a method, including:

electronically receiving a medication code representative of a plurality of medications; and electronically generating an adverse drug reaction (ADR) warning based on the medication code.

In an embodiment, the generating of the warning is performed without receiving any information indicative of an identity of a patient who takes the plurality of medications.

In an embodiment, receiving the code includes receiving the same code with respect to two patients who each take the same plurality of medications.

In an embodiment, the medication code is representative of the plurality of medications and of background medical information of a patient, and wherein generating the warning includes generating the warning based on both the plurality of medications and the background medical information.

There is further provided, in accordance with an embodiment of the invention, apparatus, including:

an adverse drug reaction (ADR) control server including a processor and a data port, the server configured to:

(a) in a first interaction with a user, receive from the user, via the data port, a list of one or more current medications; and send to the user a first medication code responsively to the list;

(b) in a second interaction with the user, receive the first medication code from the user and an indication of a new medication;

(c) access, by the processor, the list of one or more current medications based on the received first medication code, and generate an adverse drug reaction (ADR) warning based on the list of one or more current medications and the new medication; and (d) send the user a new medication code based on the list of one or more current medications and the new medication.

There is yet further provided, in accordance with an embodiment of the invention, apparatus, including:

an adverse drug reaction (ADR) control server including a processor and a data port, the server configured to:

receive, via the data port, a medication code representative of a plurality of medications; and generate, by the processor, an adverse drug reaction (ADR) warning based on the medication code.

There is still further provided, in accordance with an embodiment of the invention, apparatus, including:

an adverse drug reaction (ADR)-indicating computer, including:

a detector, configured to detect an indication of the identity of a medication;

an input unit, configured to receive a medication code from a user; and an output unit, wherein the computer is configured to be in electronic communication with a remote server, to send the medication code and the identity of the medication to the remote server, to receive an ADR alert from the remote server in response to the medication code and the identity of the medication, and to drive the output unit to alert the user in response to the received ADR alert.

In an embodiment, the detector includes a detector selected from the group consisting of: a barcode detector, and an RFID detector.

There is also provided, in accordance with an embodiment of the invention, a method, comprising:

electronically detecting an indication of the identity of a medication;

electronically receiving a medication code from a user;

sending the medication code and the identity of the medication to a remote server;

receiving an ADR alert from the remote server in response to the medication code and the identity of the medication; and alerting the user in response to the received ADR alert.

The present invention will be more fully understood from the following detailed description of embodiments thereof, taken together with the drawings, in which:

DESCRIPTION OF EMBODIMENTS OF THE INVENTION

Figure 1A:
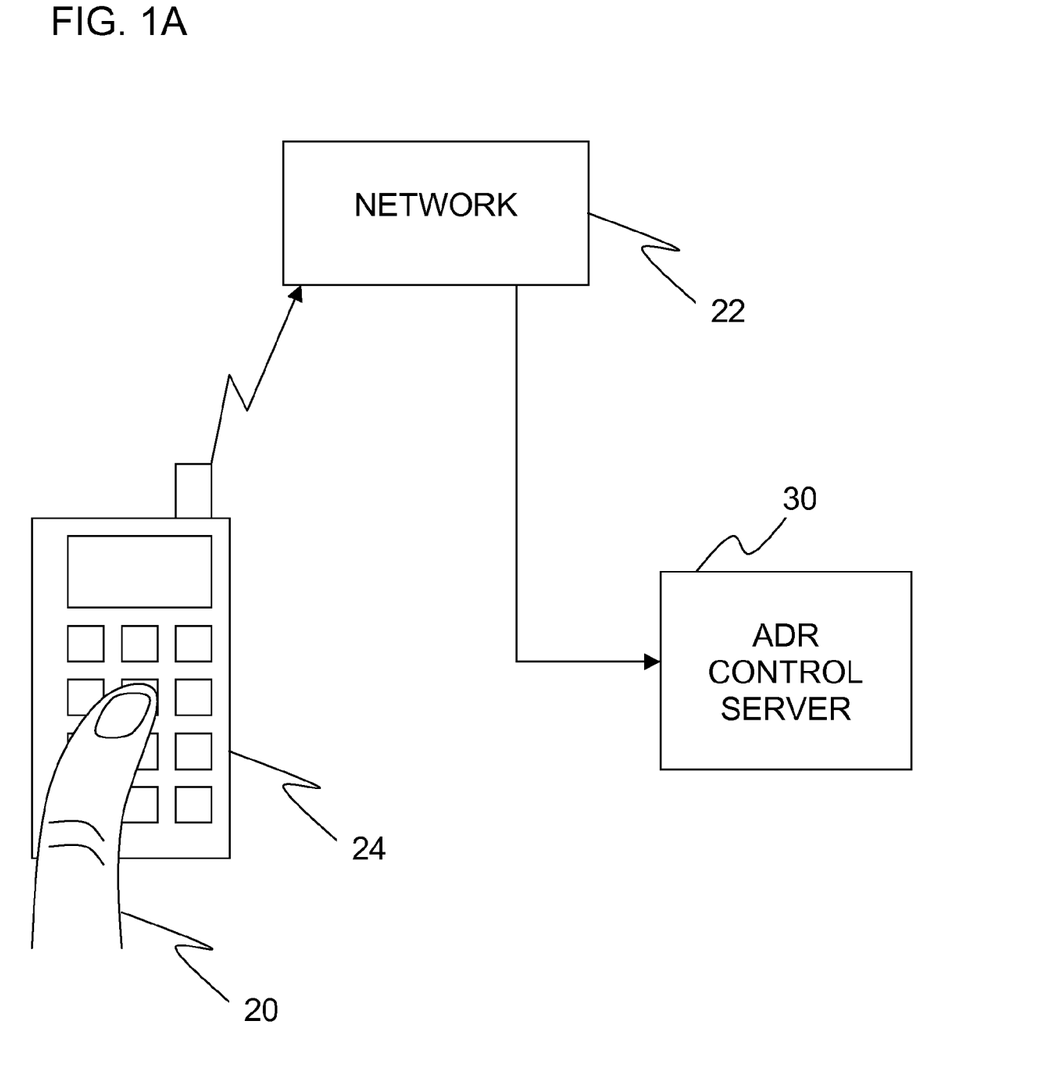
FIGS. 1A and 1B are schematic illustrations of a system for reducing adverse drug reactions (ADRs), in accordance with an embodiment of the present invention.
Figure 1B:
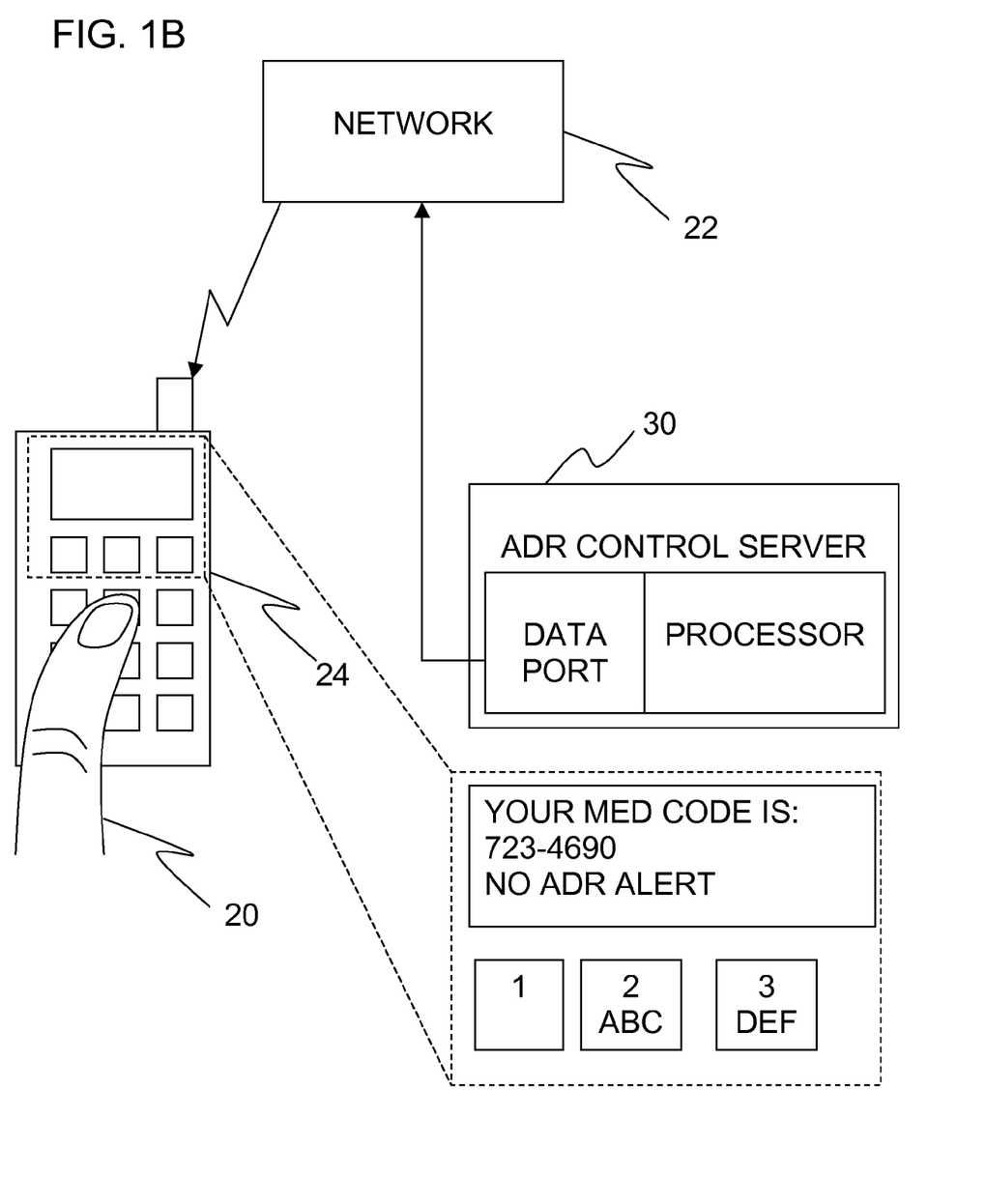

Reference is now made to FIGS. 1A and 1B, which are schematic illustrations of a system for reducing adverse drug reactions (ADRs), in accordance with an embodiment of the present invention. In some embodiments of the present invention, a user 20 enters a list of prescription and/or over-the-counter medications via an input device 24, over a network 22, into an adverse drug reaction (ADR) control server 30. The user may be, for example, a patient, a healthcare provider such as a physician, a pharmacist, or a salesperson. The list typically includes one or more medications currently being taken by the patient, and in some instances one or more medications that are proposed to be prescribed to the patient. The server receives the list (FIG. 1A), generates or retrieves a medication code representing the list of medications, and outputs the medication code to the user (FIG. 1B). The server comprises suitable hardware and software to carry out the tasks described herein, such as a processor, a data port, and a memory. The medication code is typically fairly simple (e.g., 723-4690, or 161-TAT), and, for example, can be written down and carried by the patient on a card in his wallet, or stored electronically in a memory such as a cell phone or PDA memory.

In addition, server 30 typically accesses an ADR database in order to determine whether to generate an advisory message indicative of a potential adverse drug reaction, or to generate another advisory message (e.g., "consult a healthcare professional regarding drugs X and Y," "no adverse reaction known from these medications," or "a potentially severe (or mild) adverse drug reaction has been identified between drugs X and Y").

Figure 2:
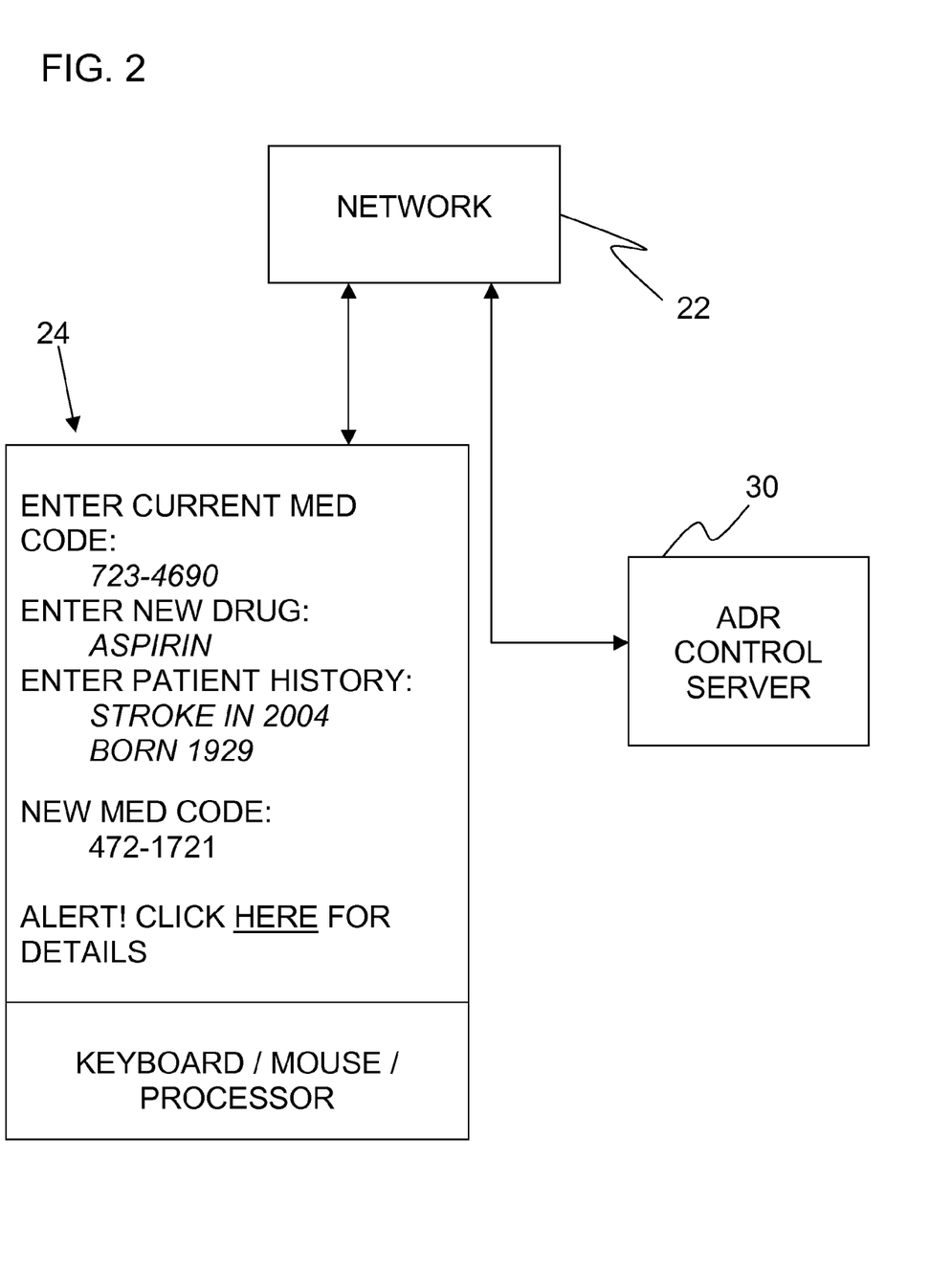
FIG. 2 is a schematic illustration of an application of the system of FIG. 1, in accordance with an embodiment of the present invention.

FIG. 2 is a schematic illustration of the system for reducing adverse drug reactions, in use following generation of the medication code as described with reference to FIGS. 1A and 1B, in accordance with an embodiment of the present invention. If the patient or physician wants to add another medication to the patient's medication regimen, the patient's medication code is sent to server 30 (rather than the entire list of medications), as well as the name of the proposed new medication. A new medication code (e.g., 472-1721) is generated or retrieved based on the original list of medications and the new proposed medication, and an advisory message is given to the patient based on the new list of medications.

It is noted that server 30 is typically not given any identifying information regarding the particular identity of the patient, such as name, address, or social security number. For some applications, however, the server may be given certain background medical information about the patient's medical condition or history, such as gender, year of birth, whether the patient is or may become pregnant, allergies, or general family or personal medical history (e.g., history of diabetes or heart disease). Thus, even when the patient or physician has entered the medications (e.g., aspirin, Lipitor) and background medical information (e.g., male, 1967, allergic to penicillin), insufficient information is available to a company managing the server or any entity that intercepts data moving to and from the server to enable a determination of the identity of the patient. In this manner, patient privacy is maintained. This technique for maintaining patient privacy notwithstanding, for some applications patients are given the option to enter identifying information (e.g., name, address and/or social security number) in order to enable the ADR control server to access the patient's medical records or for other reasons.

In a typical scenario, a doctor visits the home of a patient who already has a medication code. (Alternatively, the patient visits the doctor's office, or sees the doctor at another location.) The doctor examines the patient, inquires about the patient's medical history, and, typically, asks the patient regarding medications the patient is taking. It is noted that use of the medication code, as provided by these embodiments, does not require the patient to remember all of the medications, or to be in a medical condition to relay this information to the doctor. In this case, the doctor can access the list of the patient's current medications by sending the medication code to ADR control server 30. The doctor may decide that a new medication is suitable to treat a diagnosed condition of the patient. Instead of entering all of the medications that the patient is currently taking into an ADR database in order to determine whether there is a potential conflict with the new medication, the doctor simply sends the patient's medication code (if it has not already been sent to the ADR control server), as well as the name of the new medication to the ADR control server, and receives a new medication code as well as any drug reaction information (e.g., an alert) that the ADR control server may send. If the doctor chooses to prescribe the new medication based on the information received from the ADR control server (or, in some cases, despite the received information), then the patient writes down the new medication code on his card, and takes a prescription from the doctor to a pharmacy to receive the new medication. For some applications, the pharmacy will itself check for adverse drug reactions, by inputting to the ADR control server the patient's new medication code, which now also represents the new medication.

If, on the other hand, the doctor reviews the information from ADR control server 30 and chooses not to prescribe the medication, then she may instead enter the patient's original medication code, and another medication suitable for treating the diagnosed condition. The server sends a new medication code, and issues any indications as appropriate regarding adverse drug reactions. Alternatively or additionally, the server suggests a list of one or more substitute medications that do not generate any conflict messages based on the patient's medication code, and that are sometimes used in place of the medication that generated an ADR warning. (It is clearly the doctor's responsibility to evaluate whether the proposed substitute medications are suitable for treating the patient's diagnosed condition.)

In some embodiments, data are passed to and from ADR control server 30 via normal telephone communications, and input device 24 comprises a telephone (FIGS. 1A and 1B). Typically, the patient (or healthcare provider) generates an initial medication code by entering a list of the patient's current medications using normal touch-tone telephone functionality. For example, using the system in which ABC is the 2 button, DEF is the 3 button, etc., the patient enters "aspirin" by typing 2774746. Assuming that the ADR control server only knows one medication with the numerical representation 2774746, it sends a spoken message: "You entered aspirin. Press 1 to confirm and move on, 2 to enter dosage, or 3 to reenter." If two or more medications both have the same representation, then the ADR control server responds: "Press 1 if the drug is drug-1; press 2 if the drug is drug-2; . . ." To minimize data entry errors, a request for confirmation of the drug name typically follows the patient's choice in every case.

At the end of entering all of his medications, or at any time subsequently thereto, the patient can query ADR control server 30 to dictate a list of all of his medications. If at some point the patient discontinues a medication, normal telephone menu functionality is employed to allow the patient to remove the discontinued medication from the medication code, and to receive a new medication code representing the reduced list of medications currently taken by the patient.

The patient is similarly typically able to enter background medical information as described hereinabove (e.g., gender, year of birth, allergies, state of pregnancy, personal or family history) using normal telephone menu functionality, and to receive a medication code based on the list of medications and the background medical information.

In some embodiments, the user (typically the patient or doctor) interacts with ADR control server 30 via a website or a program running on a standard personal computer or hand-held computer (i.e., a PDA), which allows entry of a list of medications and outputs a medication code and, if appropriate, informational messages or alarms regarding the list of medications. In this case, input device 24 comprises the computer (FIG. 2).

Regardless of the method by which the user interacts with ADR control server 30, a medication code is typically delivered to user 20 immediately, and, if the user chooses, sent to an address the user chooses (such as a postal address, an e-mail address, a cell phone by SMS, etc.). For some applications, the user selects a long-term storage code that he will be able to remember (e.g., "romeojuliet"), and designates that the ADR control server also saves the medication code (or the list of medications and background information) in a manner that it can be accessed by the user upon entering the long-term storage code. If no personal identifying information is disclosed to the ADR control server at the time of selection of the long-term storage code, then patient privacy is maintained.

Typically, any warnings or informational messages that are generated are sent by ADR control server 30 every time that a user interacts with the ADR control server, or, alternatively, every time that any change is made to the medication code. Warnings may include, for example:

"Drug-1 and drug-2 are known or suspected to produce an adverse drug reaction that is mild (alternatively, for example: moderate, severe)"

"Drug-1 at the dosage entered is known or suspected to produce a minor adverse reaction in diabetic patients"

"Drug-1 is known or suspected to produce a life-threatening allergic reaction in patients who are allergic to some form of antibiotics"

"Drug-1 and drug-2 are known or suspected to induce hemorrhage (alternatively, for example: lower blood pressure, induce coronary spasm)"

Combinations of the warnings above may be generated, as well. Alternatively or additionally, other drug warnings known in the art are generated.

In order to send a new user a medication code based on a new list of medications, in some embodiments, an algorithm executed by ADR control server 30 receives the list of medications, and checks whether an identical list has already been entered. For example, the new user may enter Tylenol and Xanax. If this particular combination of medications has ever been entered before, then the ADR control server sends the user the same medication code corresponding to the two drugs Tylenol and Xanax that was sent to the one or more prior users who had also entered these two drugs. If, on the other hand, the new user is the first to enter these two drugs, then the ADR control server assigns a new medication code to permanently represent these two drugs, and sends this new code to the user. Any future user who enters Tylenol and Xanax as his list of medications will receive the same medication code. Similarly, if the user had entered personal medical background information as well (e.g., male, year of birth 1939, non-insulin-dependent diabetes), then a new medication code would have been generated in the same manner, in this case representing: (a) medications—Tylenol and Xanax, and (b) background information—male, 1939, non-insulin-dependent diabetes.

A range of strategies for assigning new medication codes will occur to a person of ordinary skill in the art who has read the present patent application. For example, the first medication code assigned could be 100-0000, and may represent the medication Synthroid and the background information female and allergic to pollen. (This would be because the first user to request a medication code chose to report this medication and these characteristics, rather than because of any particular pharmaceutical characteristic of the medication.) Based on information sent by a second user, the second medication code assigned could be 100-0001, for Paxil, and does not represent any background information because the user did not enter any such information. The third medication code would be 100-0002, representing Zocor 20 mg, aspirin 100 mg, Zomig 2.5 mg; male, 1943, family history of heart disease and migraines. The fourth code, 100-0003, representing Zocor 10 mg and Paxil, is typically assigned independently of the fact that previous codes also represented the drugs Zocor and Paxil, but in different combinations. If, at this point, a user enters medication code 100-0002 and indicates that he wants to remove aspirin from the list, a new medication code (100-0004) would be assigned, representing Zocor 20 mg, Zomig 2.5 mg; male, 1943, family history of heart disease and migraines.

To minimize errors, a checksum or other digit or technique is typically included in the medication code, e.g., as the last digit.

For some applications, in order to conserve the number of medication codes that are assigned, drugs that have multiple names and/or are in a common family are represented together. Thus, for example, Aceril, captopril, convertin, Enaladex, enalapril, Tritace, and Vascase all belong to the ACE inhibitors group (angiotensin-converting-enzyme inhibitors), and, for some applications, are represented using a common representation. Similarly, Normiten, atenolol, Concor, Dimitone, Deralin, Lopressor, Normalol, and Prolol all belong to the beta-blockers group, and may be represented using a common representation. Alternatively or additionally, dosages are represented collectively (for example, Zocor 10 mg and Zocor 20 mg may be assigned the same medication code, and this may be different from Zocor 30 mg). Further alternatively or additionally, patients' background information may be represented collectively, such as by rounding birth years to the nearest multiple of five. Typically, a single medication code represents both the generic name of a drug (e.g., acetaminophen) and a brand name associated with the drug (e.g., Tylenol).

Figure 3:
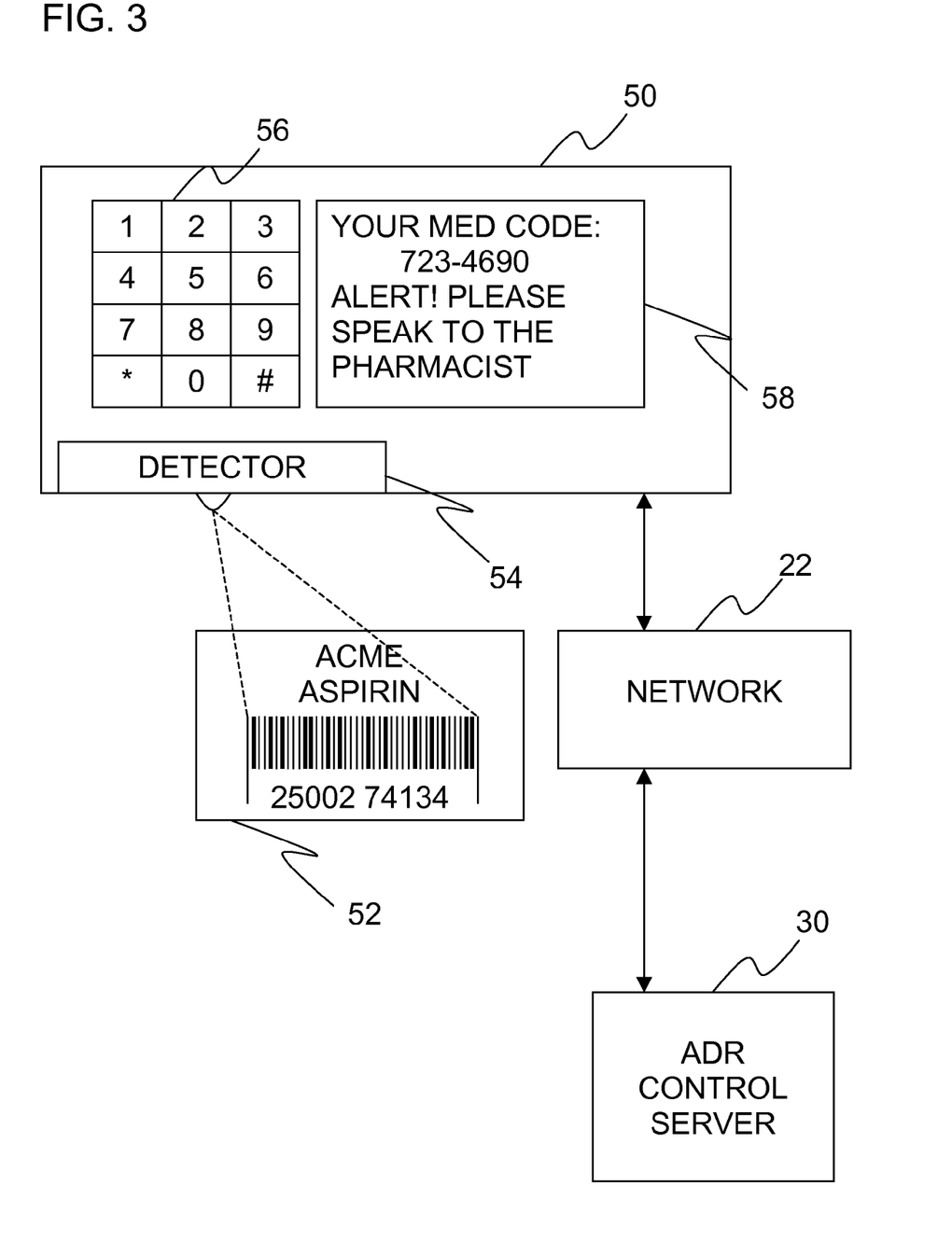
FIG. 3 is a schematic illustration of an application of the system of FIG. 1, in accordance with another embodiment of the present invention.

Reference is now made to FIG. 3, which is a schematic illustration of the system for reducing adverse drug reactions, in accordance with another embodiment of the present invention. An on-line or physical pharmacy allows a user contemplating a purchase of a new prescription or over-the-counter medication 52 to convey to server 30 a medication code representing his current medications, as well as the name or another indication of the identity of the new medication. For example, a dedicated ADR-indicating computer 50 may comprise a detector 54 (e.g., a barcode reader or an RFID scanner), an input unit 56 (e.g., a keypad or a reader of a magnetic card or a smart card), and an output unit 58, such as a screen or other visual or audible output device. ADR-indicating computer 50 is placed near the checkout counter in a physical pharmacy, and the user enters his medication code into input unit 56, and waves new medication 52 in front of detector 54 (or otherwise indicates the identity of the new medication). A response is generated by ADR control server 30, and conveyed via output unit 58, indicating whether a possible adverse drug reaction has been identified.

For online pharmacies, the user could be prompted for his medication code at the time of clicking "add to my basket" with respect to a particular medication. For some applications, simple messages aimed at consumers with no medical background reduce the likelihood of adverse drug reactions. For example, an output consisting of green (drug combination is approved), yellow (consult your doctor), or red (do not take this drug) is typically sufficient to achieve a substantial reduction in adverse drug reactions. Optionally, a request can be entered by an interested user to receive additional information from ADR control server 30.

Figure 4:
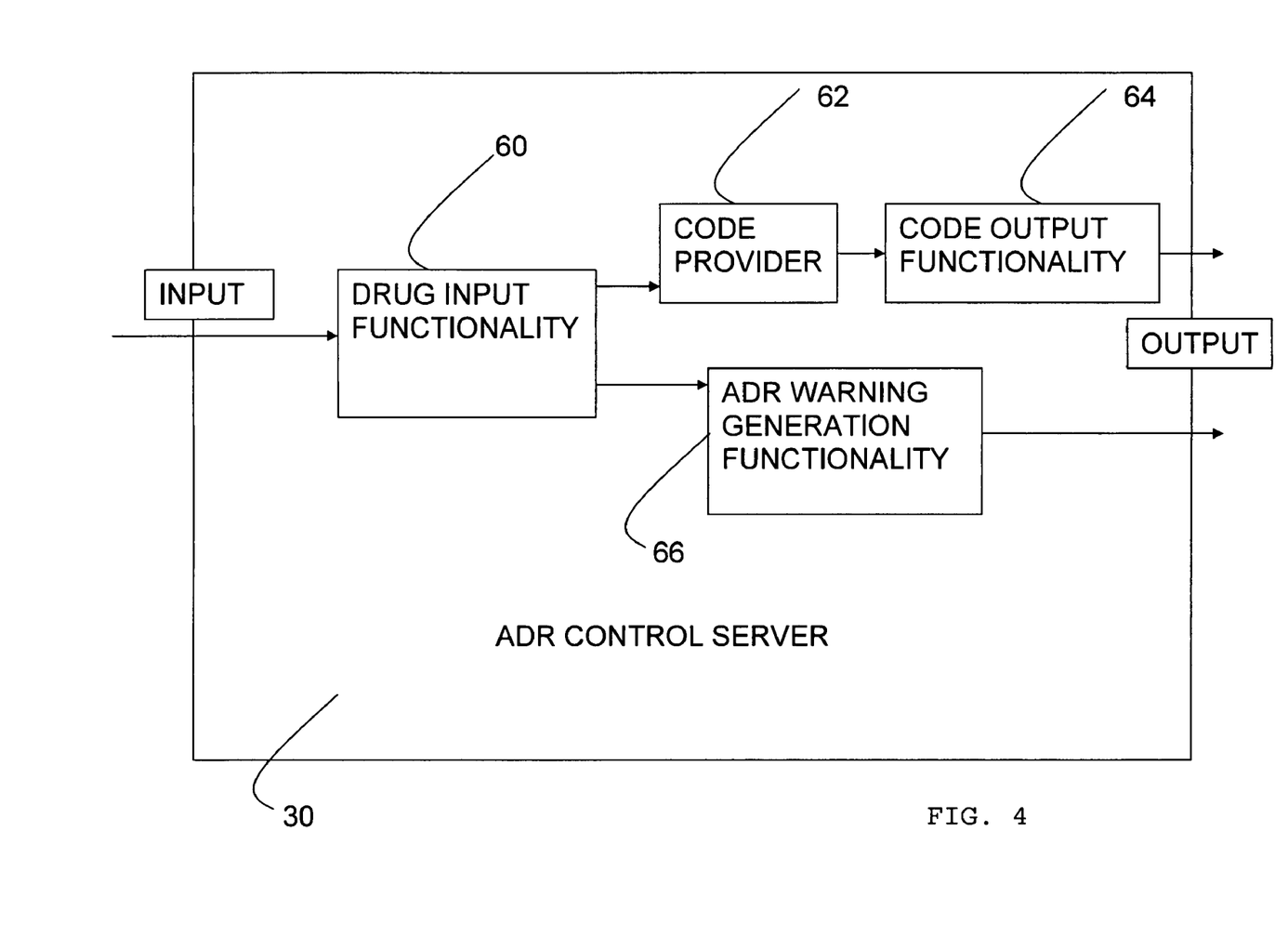
FIG. 4 is a schematic illustration of a control server, in accordance with an embodiment of the present invention.

Reference is now made to FIG. 4, which is a schematic illustration of control server 30, in accordance with an embodiment of the present invention. Control server 30 typically includes drug input functionality 60 for receiving information regarding medications that are currently being taken, and/or proposed to be taken by the patient. For example, the server may receive a list that includes one or more medications that are currently being taken by the subject. The control server also includes a code provider 62 that provides a code representing a list of medications, as described herein. For example, the code generator generates the code, or retrieves the code from a database. The control server further includes code output functionality 64 for sending the code from the server to the user. In addition, the control server includes ADR warning generation functionality 66 for determining whether to generate an advisory message indicative of a potential adverse drug reaction, or to generate another advisory message, as described herein. In response to determining that an ADR warning should be generated, the ADR warning generation functionality sends the ADR warning to the user.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for using a server to generate an advisory message to a user, comprising:
   receiving, by the server, a first list, said first list including medications currently being taken by a patient;
   generating, by the server, a first code, said first code representing said first list of medications currently being taken by the patient, but not disclosing an identification of individual elements of said list;
   sending by the server said code;
   thereafter:
   receiving, by the server, from the user:
      said first code, and
      an identification of at least one additional medication proposed to be taken by the patient;
   determining, by the server, whether an adverse drug reaction warning should be generated, the adverse drug reaction warning indicating a potential danger of concurrent administration to the patient of: (a) at least one medication from said list of medications currently being taken by the patient and (b) the additional medication proposed to be taken by the patient;
   sending the adverse drug reaction warning, by the server, in response to determining that The adverse drug reaction warning should be generated;
   generating, by the server, a second code, said second code being different from said first code, and said second code representing a second list, said second list including the medications currently being taken by the patient and the additional medication proposed to be taken by the patient, but said second code not disclosing an identification of individual elements of said second list; and
   sending said second code to the user from the server.

2. The method according to claim 1, wherein sending the first code to the user comprises determining whether a code already exists with respect to the first list, and, if so, sending the already-existing code to the user, and, if not, generating the first code and sending the generated first code to the user.

3. The method according to claim 1, wherein generating the first code comprises generating the code not responsively to a pharmaceutical characteristic of at least one of the current medications.

4. The method according to claim 1,
   wherein receiving the first list from the user comprises receiving an indication of a dosage of at least one of the medications currently being taken by the patient,
   wherein sending the first code comprises sending the first code responsively to the first list and the dosage,
   and
   wherein determining, by the server, whether an adverse drug reaction warning should be generated, comprises determining whether the adverse drug reaction warning should be generated based on the first list, the additional medication, and the dosage.

5. The method according to claim 4, wherein sending the first code responsively to the received indication of the dosage comprises:
   if the dosage is near a dosage of the one of the medications currently being taken by the patient for which a code has already been generated, sending as the first code the same code that has already been generated; and
   if the dosage is not near a dosage of the one of the medications currently being taken by the patient for which a code has already been generated, sending as the first code a code different from the code that has already been generated.

6. An adverse drug reaction control system for generating an adverse drug reaction warning to a user, comprising:
   a computer including drug-input functionality that receives a first list, said first list including medications currently being taken by a patient;

a code generator that generates a first code, said first code representing said first list of medications currently being taken by the patient, but not disclosing an identification of individual elements of said list;

code-output functionality; and adverse drug reaction warning generation functionality, the drug-input functionality receiving from a user, following generation of the code, the first code and an identification of at least one additional medication proposed to be taken by the patient;

the adverse drug reaction warning generation functionality:
- determining whether to generate an adverse drug reaction warning indicating a potential danger of concurrent administration to the patient of: (a) a medication from said first list of medications currently being taken by the patient and (b) the additional medication proposed to be taken by the patient, and
- sending the adverse drug reaction warning to the user, in response to determining that the adverse drug reaction warning should be generated, the code generator generating a second code, said second code being different from said first code, said second code representing a second list, said second list including the medications currently being taken by the patient and the additional medication proposed to be taken by the patient, and said second code not disclosing an identification of individual elements of said second list, and the code-output functionality sending said second code to the user.

7. The system according to claim 6, wherein the code generator is configured to determine whether a code already exists with respect to the first list, and wherein,
- if so, the code-output functionality is configured to output the already-existing code, and,
- if not, the code generator is configured to generate the first code and the code-output functionality is configured to output the generated first code.

8. The system according to claim 6, wherein the code generator is configured to generate the code not responsively to a pharmaceutical characteristic of at least one of the medications currently being taken by the patient.

9. The system according to claim 6,
wherein the drug-input functionality is configured to receive an indication of a dosage of at least one of the medications currently being taken by the patient,
wherein the code generator is configured to generate the first code responsively to the list and the dosage, and
wherein the adverse drug reaction warning generation functionality is configured to determine whether to generate the adverse drug reaction warning based on the first list, the additional medication, and the dosage.

10. The system according to claim 9, wherein the code generator is configured to:
- if the dosage is near a dosage of the one of the medications currently being taken by the patient for which a code has already been generated, generate as the first code the same code that has already been generated, and
- if the dosage is not near a dosage of the one of the medications currently being taken by the patient for which a code has already been generated, generate as the first code a code different from the code that has already been generated.

* * * * *